Figure 1:
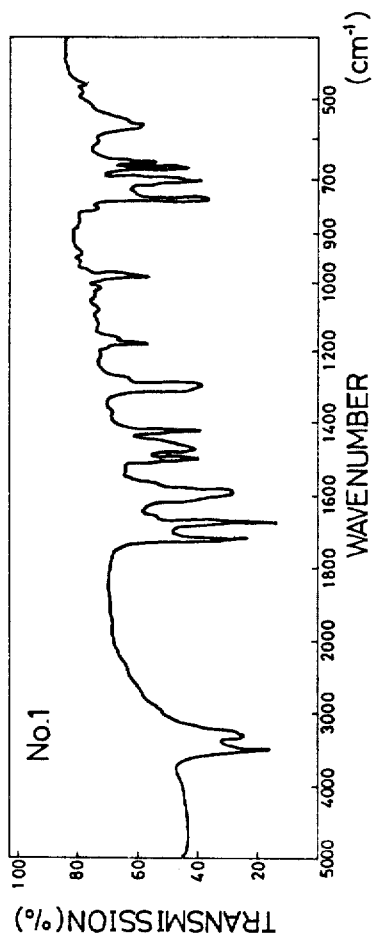

United States Patent [19]
Aoki et al.

[11] Patent Number: 4,492,597
[45] Date of Patent: Jan. 8, 1985

[54] 1,5-DIPHENYL DERIVATIVE OF 1,2,4-TRIAZOLE-3-CARBOXAMIDE AND HERBICIDE CONTAINING THE SAME

[75] Inventors: Katsumichi Aoki; Yoichi Kanda; Keigo Satake; Hiroyasu Shinkawa, all of Iwaki, Japan

[73] Assignee: Kureha Kagaku Kogyo Kabushiki Kaisha, Tokyo, Japan

[21] Appl. No.: 379,944

[22] Filed: May 19, 1982

[30] Foreign Application Priority Data

May 25, 1981 [JP]  Japan ............................. 56-77967
May 25, 1981 [JP]  Japan ............................. 56-77968

[51] Int. Cl.³ .................... A01N 43/64; C07D 249/10
[52] U.S. Cl. .................................... 71/92; 548/228; 548/262
[58] Field of Search ............................. 548/262; 71/92

[56] References Cited

FOREIGN PATENT DOCUMENTS 34481  8/1981  European Pat. Off. ............ 548/262

OTHER PUBLICATIONS

Browne et al., J. Chem. Soc., (London), 1962, pp. 575-583.
Sawdey, J. Am. Chem. Soc., vol. 79, pp. 1955-1956, (1957).
Harbash, Tetrahedron, vol. 31, pp. 25-29, (1975).
Okumura et al., Chem. Abstracts, vol. 86, Abstract No. 72658u, (1977).

Primary Examiner—Alton D. Rollins
Attorney, Agent, or Firm—Cushman, Darby & Cushman

[57] ABSTRACT

A compound of 1,5-disubstituted 1,2,4-triazole-3-carboxamide represented by the general formula:

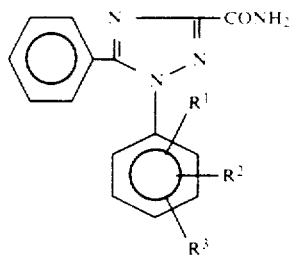

wherein $R^1$ is alkyl of one to three carbon atoms, chloro, fluoro, iodo, trifluoromethyl or nitro, $R^2$ is hydrogen, methyl or chloro, $R^3$ is hydrogen or methyl is provided in the invenfnion, which shows an excellent herbicidal activity.

11 Claims, 34 Drawing Figures

1,5-DIPHENYL DERIVATIVE OF 1,2,4-TRIAZOLE-3-CARBOXAMIDE AND HERBICIDE CONTAINING THE SAME

This invention relates to a derivative of 1,2,4-triazole, a process for preparing thereof and a herbicide containing the derivative as an active ingredient.

Certain compounds of 1,2,4-triazole derivative are known to the person skilled in the art as disclosed in for example, J. Amer. Chem. Soc., 79, 1955–1956 (1957), Tetrahedron, 31, 25–29 (1975) and J. Chem. Soc., 575–583 (1962), however in these references there are disclosed no physiological activities, in particular, herbicidal property of the compounds.

It is an object of the invention to provide a compound of 1-substituted phenyl-b 5-phenyl-1,2,4-triazole-3-carboxamide. A further object of the invention is to provide a process for preparing the compound. A still further object of the invention is to provide a herbicide containing the compound as an active ingredient.

The compound of the invention is represented by the general formula I:

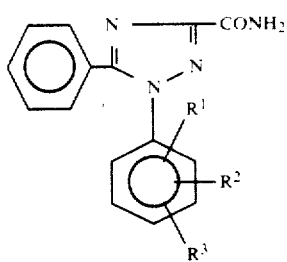

wherein $R^1$ is alkyl having one to three carbon atoms, chloro, fluoro, iodo, trifluoromethyl or nitro, $R^2$ is hydrogen, methyl or chloro, and $R^3$ is hydrogen or methyl, provided that 1-(4-methylphenyl)-5-phenyl-1,2,4-triazole-3-carboxamide is excluded.

The compound of the invention may be prepared by any appropriate and conventional method, for example, by refluxing 4-substituted phenyl-hydrazono-2-phenyl-oxazoline-5-one (represented by the general formula II as shown in the reaction scheme below) obtained by the reaction of a corresponding diazonium salt and hippuric acid in a 29% methanolic solution of ammonium hydroxide (refer to J. Amer. Chem. Soc., 79, 1956 (1957)), or by contacting a compound of the general formula II with a 29% solution of ammonium hydroxide in acetone under reflux followed by adding concentrated hydrochloric acid. These reactions are shown schematically as follows:

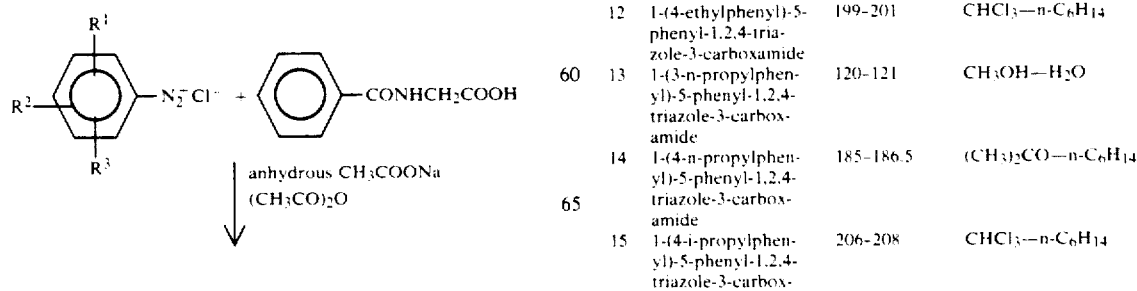

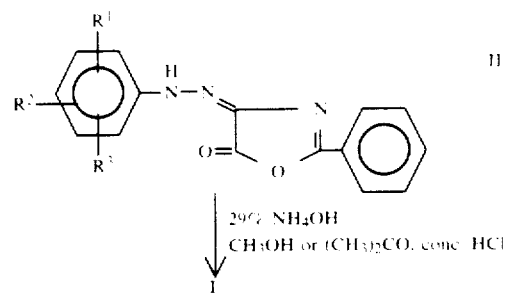

wherein $R^1$, $R^2$ and $R^3$ are defined above.

Figure 2:
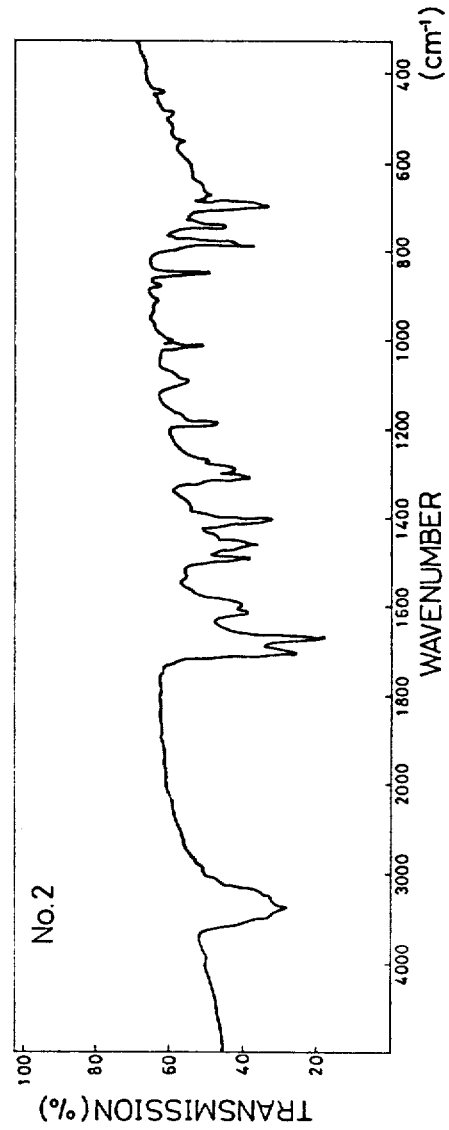
Figure 3:
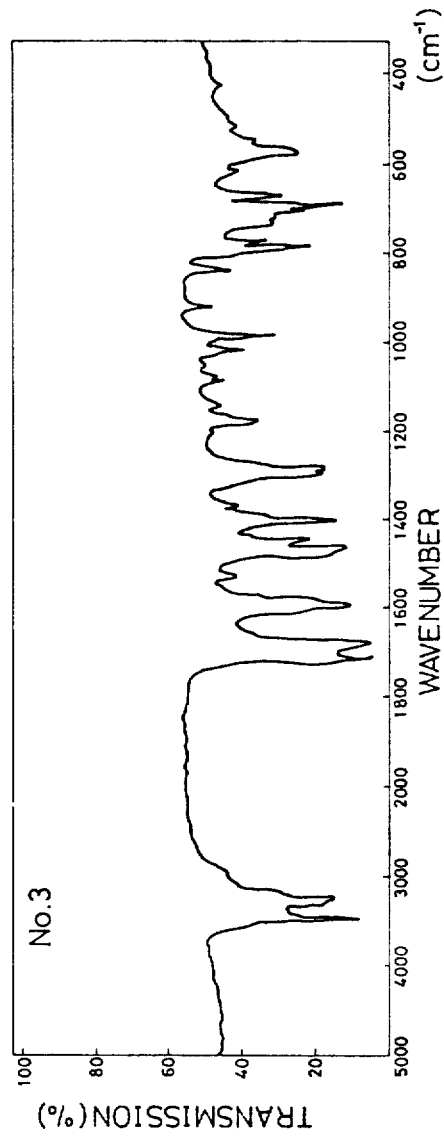
Figure 4:
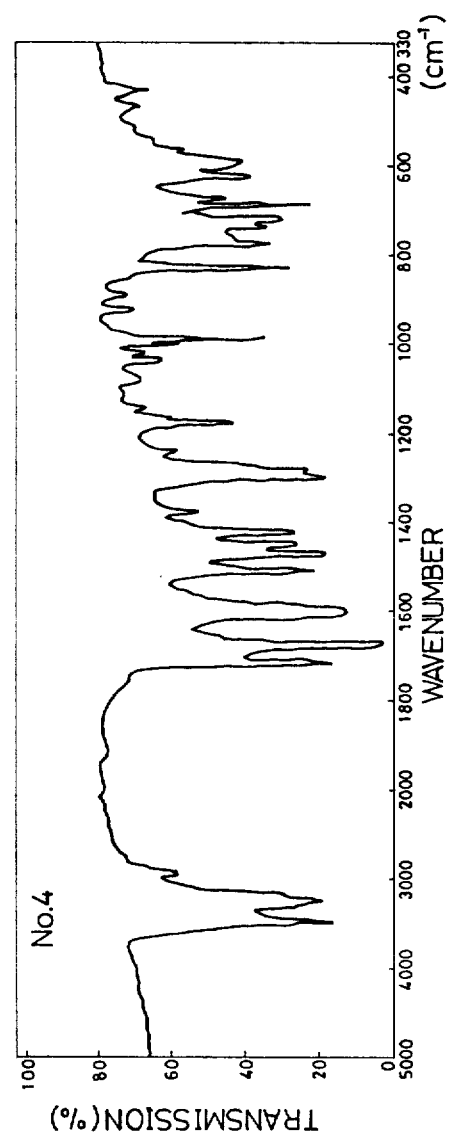
Figure 5:
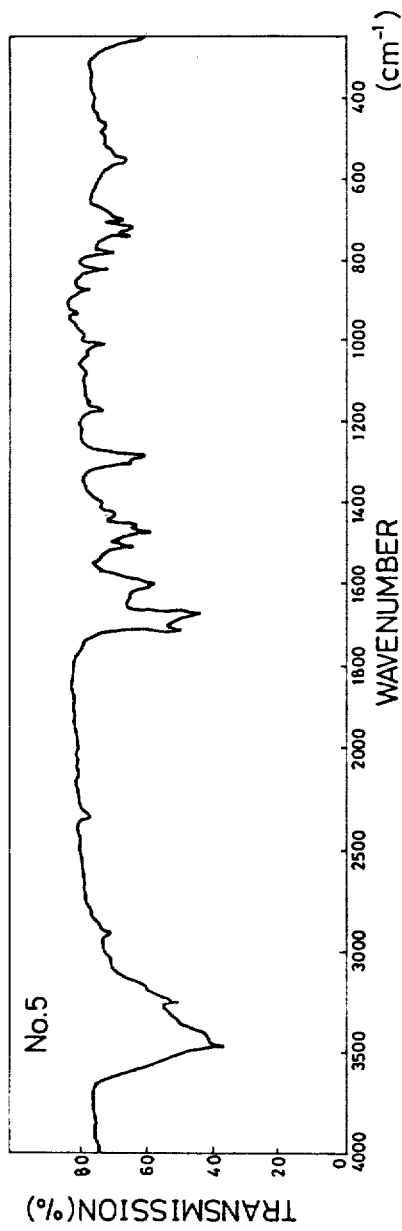
Figure 6:
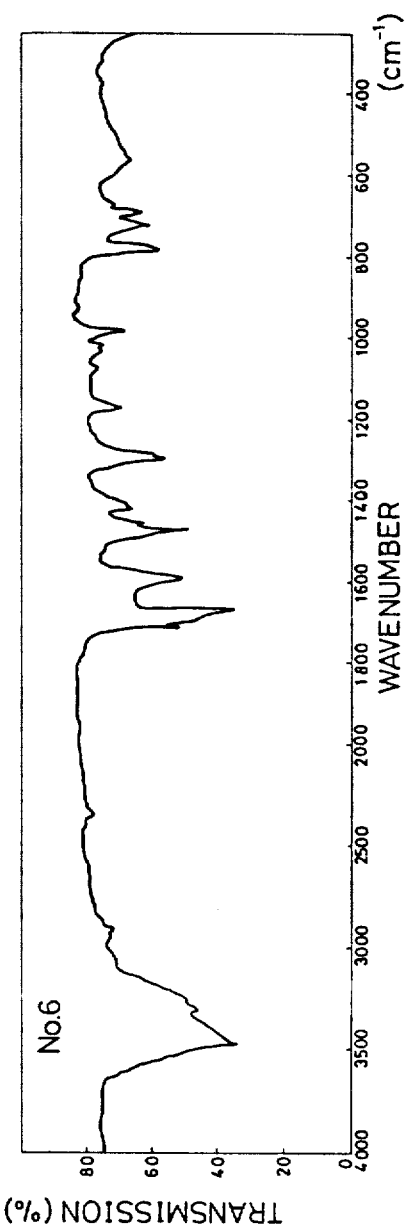
Figure 7:
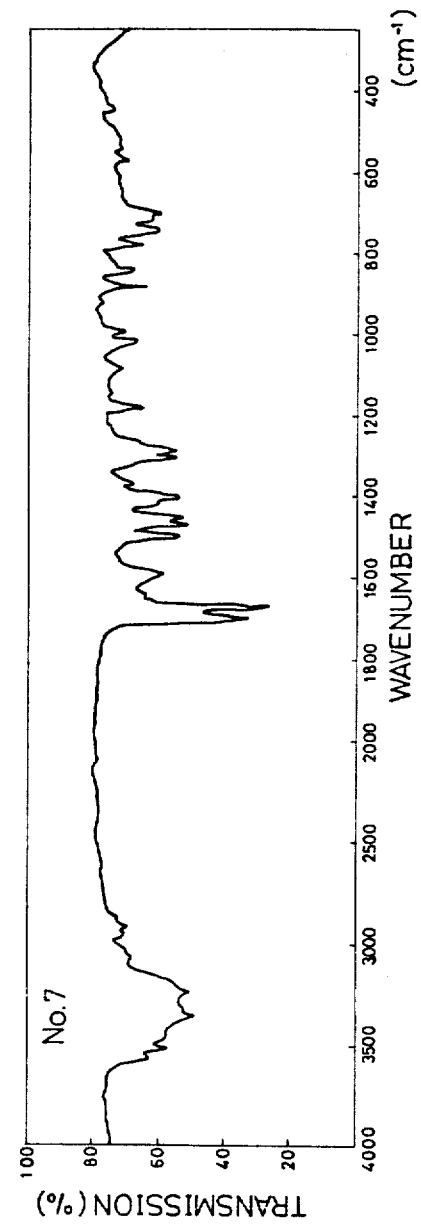
Figure 8:
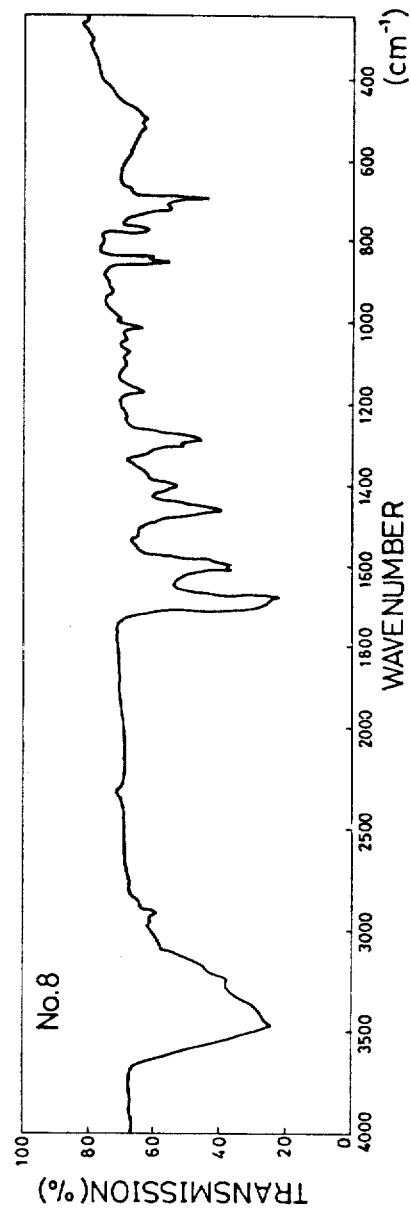
Figure 9:
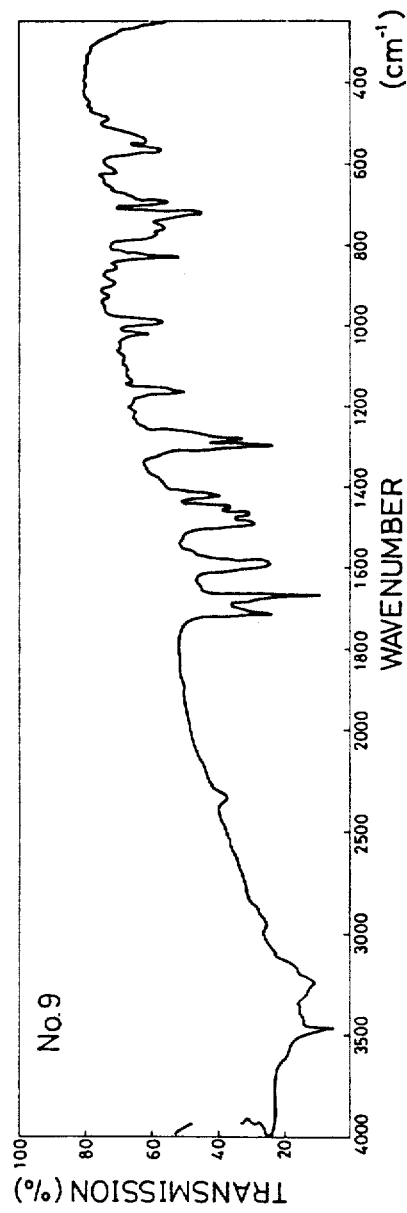
Figure 10:
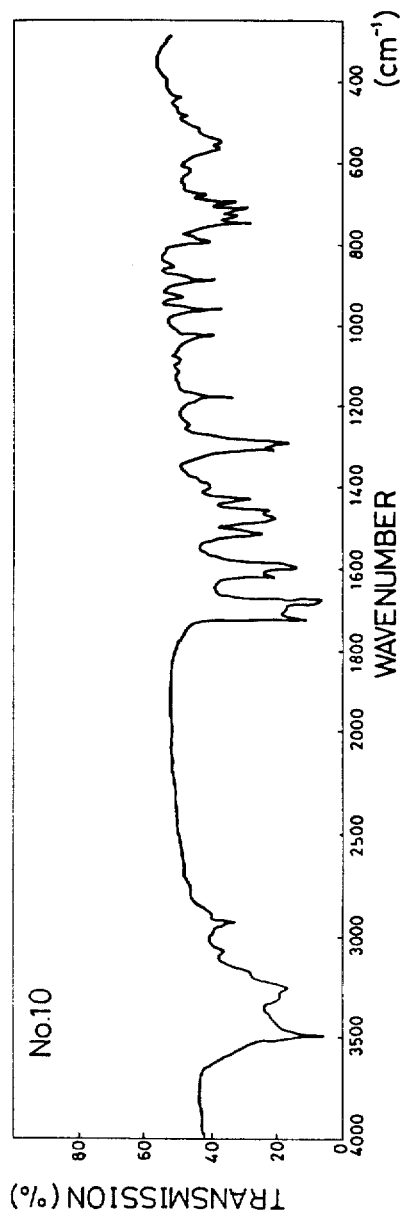
Figure 11:
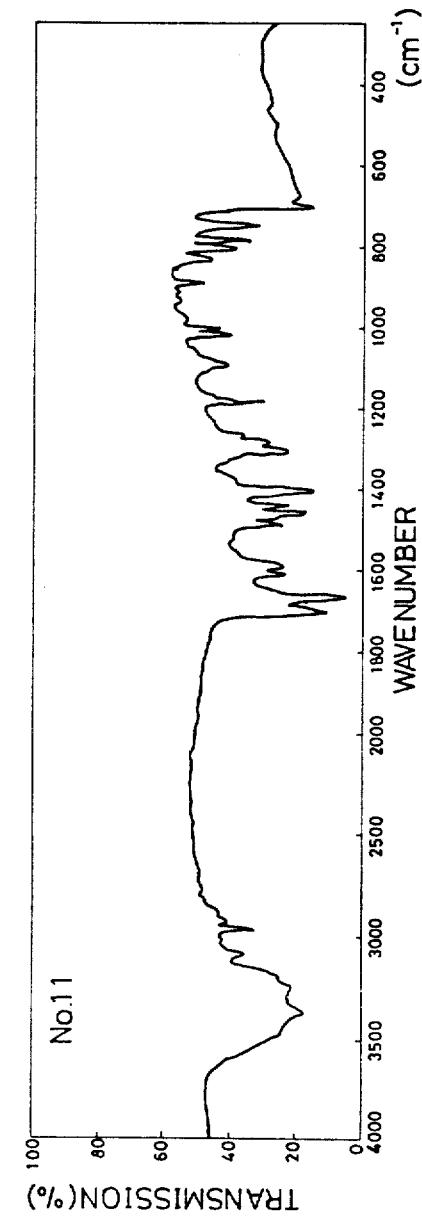
Figure 12:
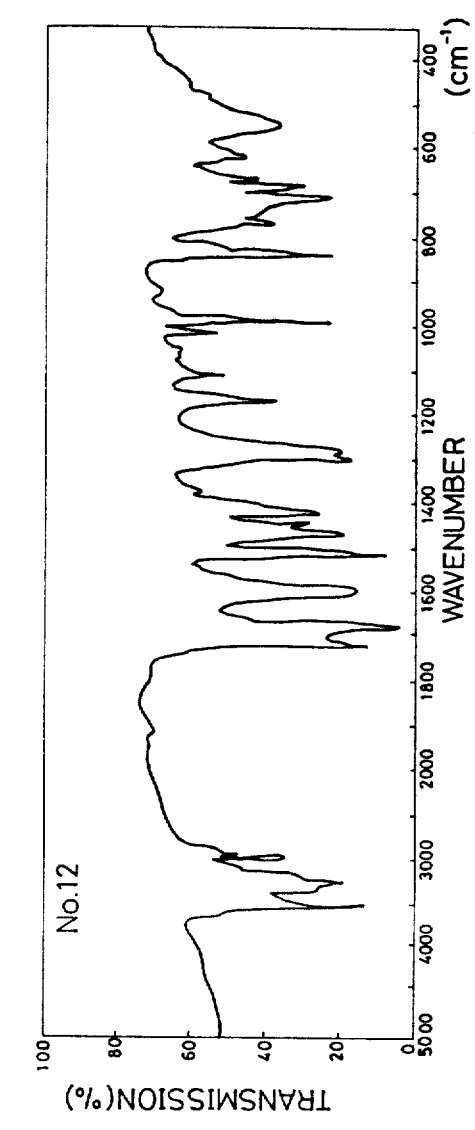
Figure 13:
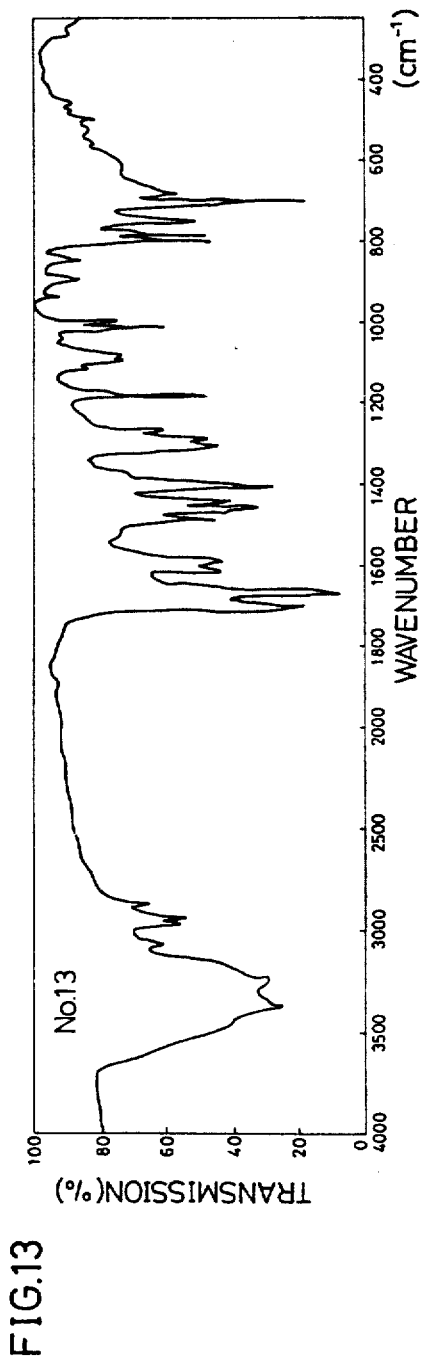
Figure 14:
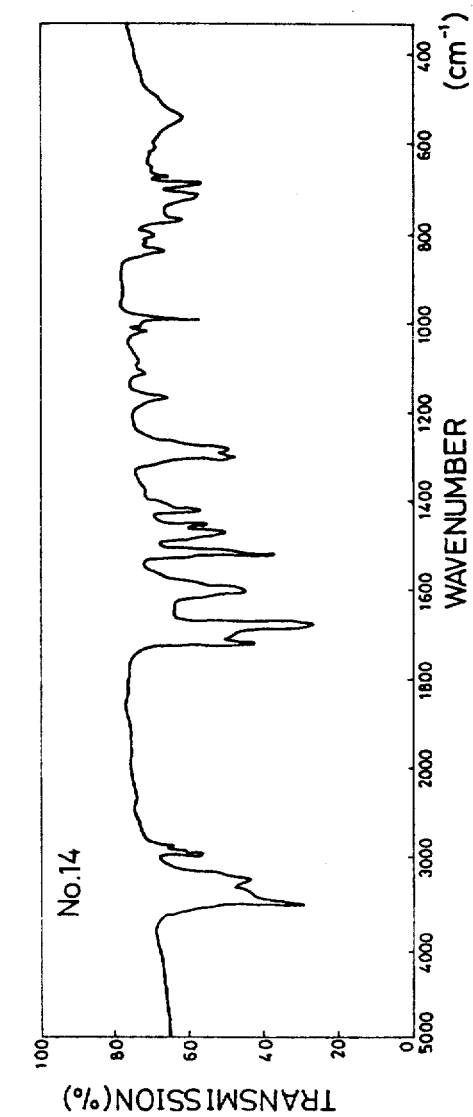
Figures 15, 16:
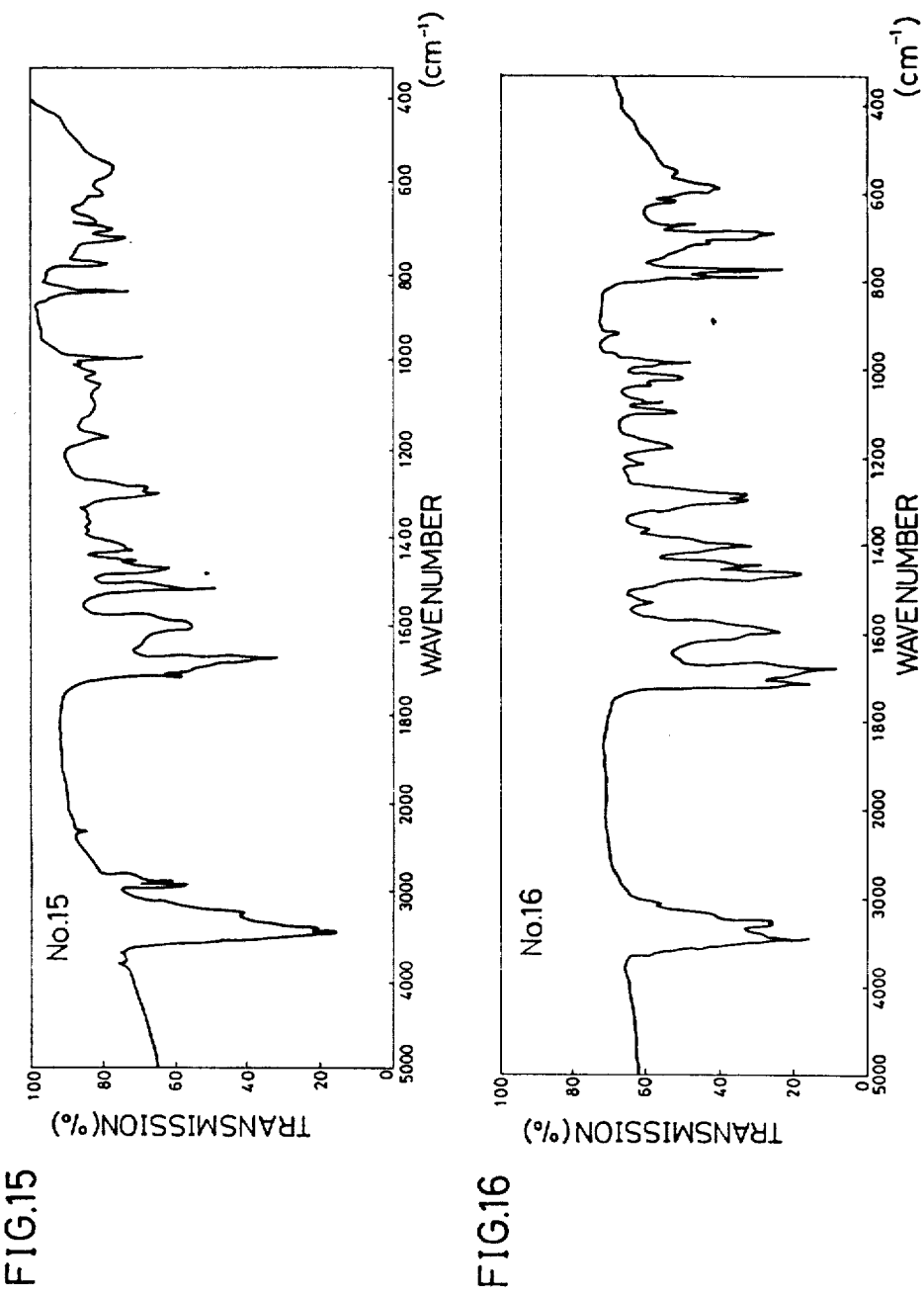
Figure 17:
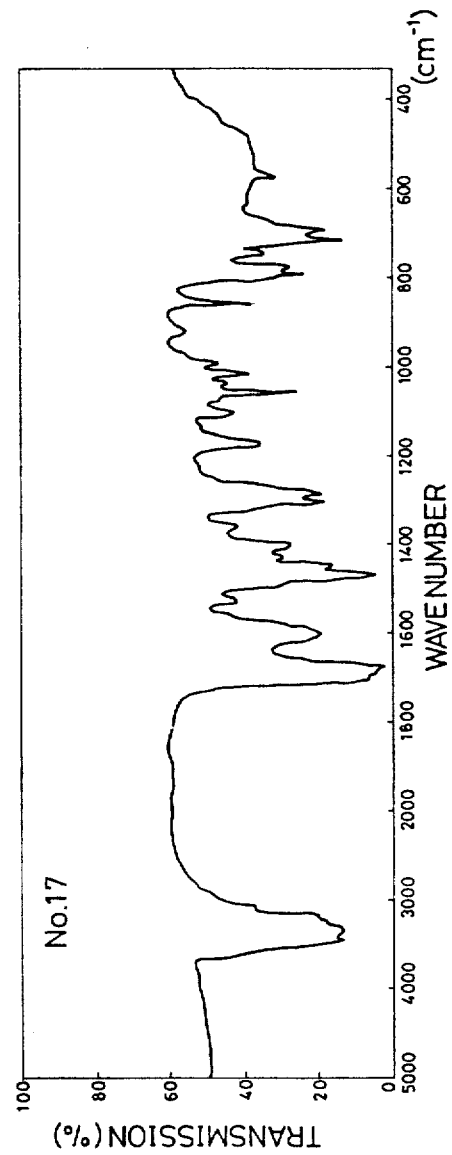
Figure 18:
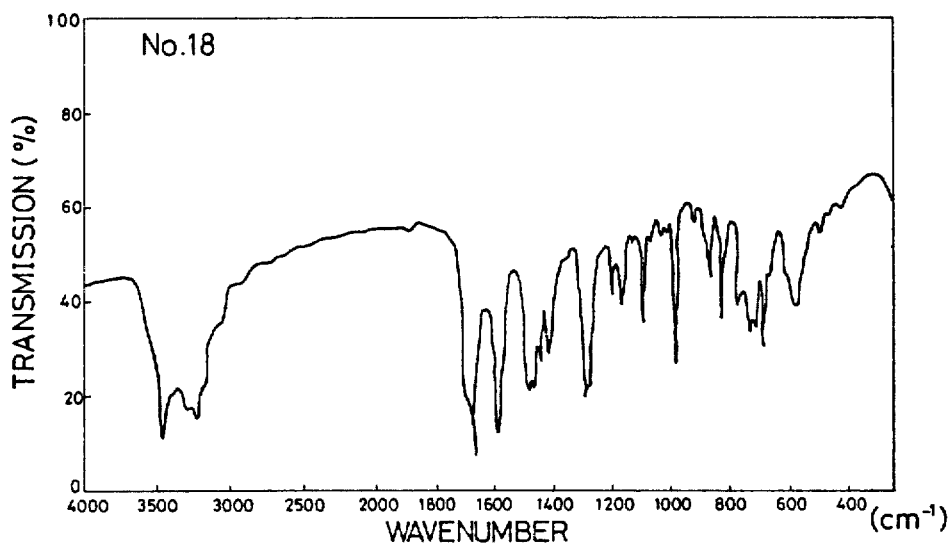
Figure 19:
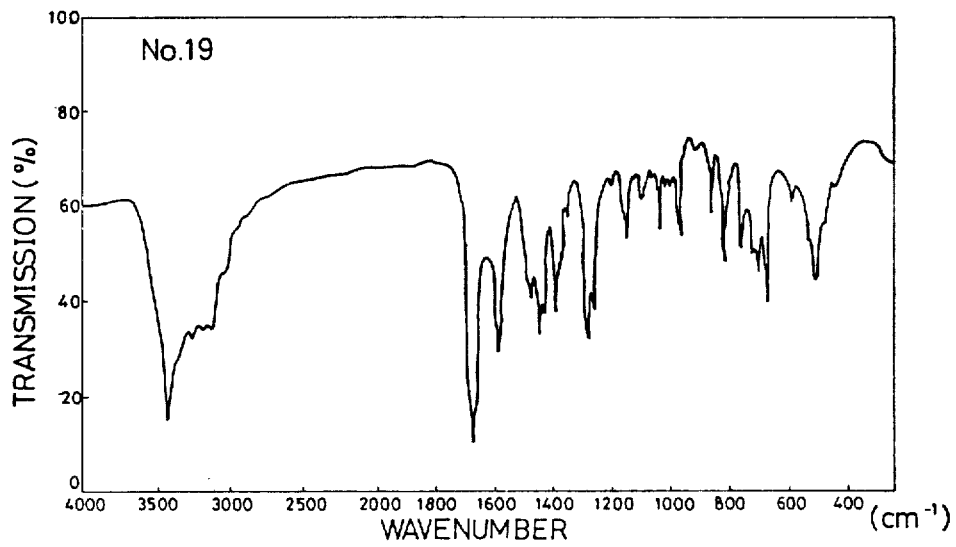
Figure 20:
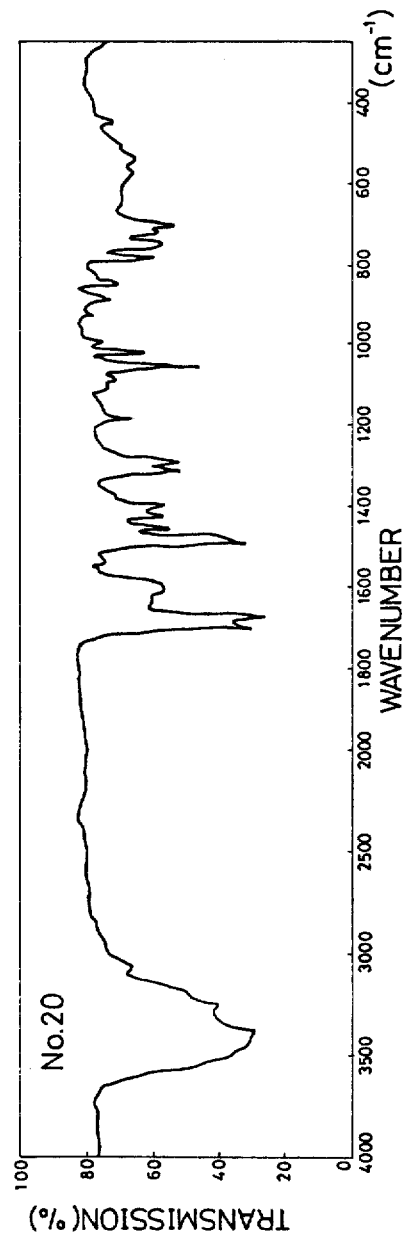
Figure 21:
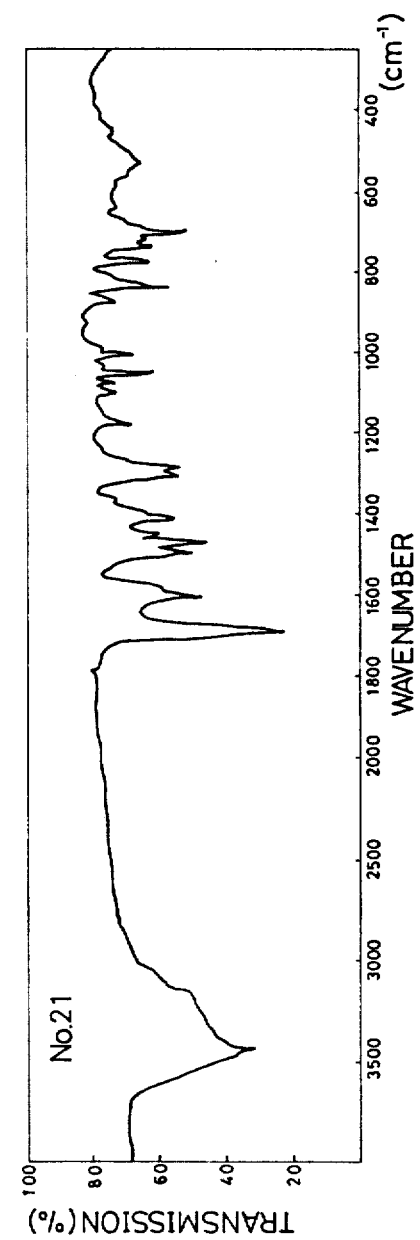
Figure 22:
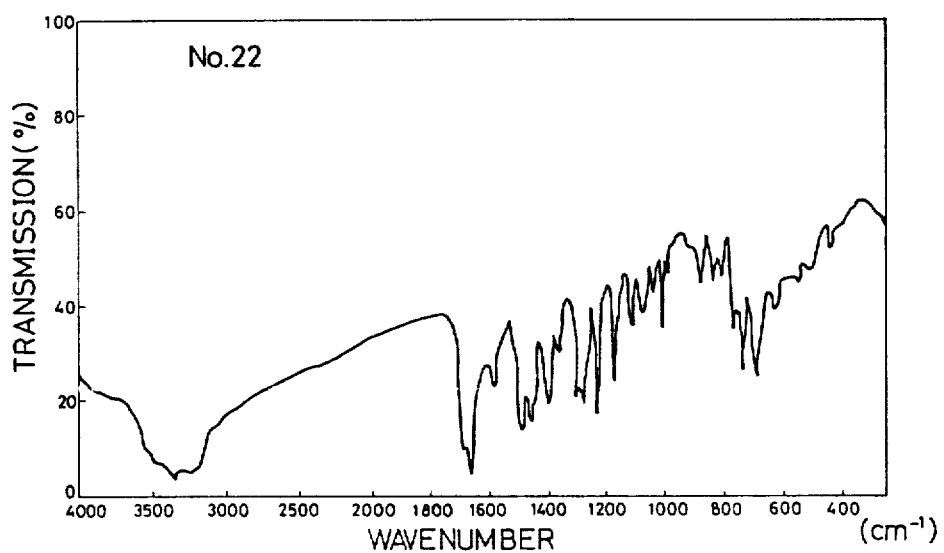
Figure 23:
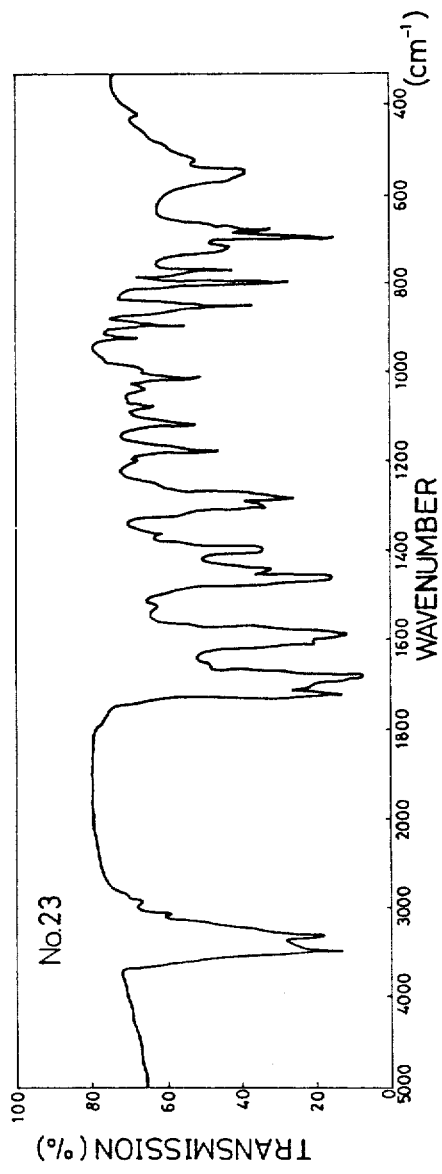
Figure 24:
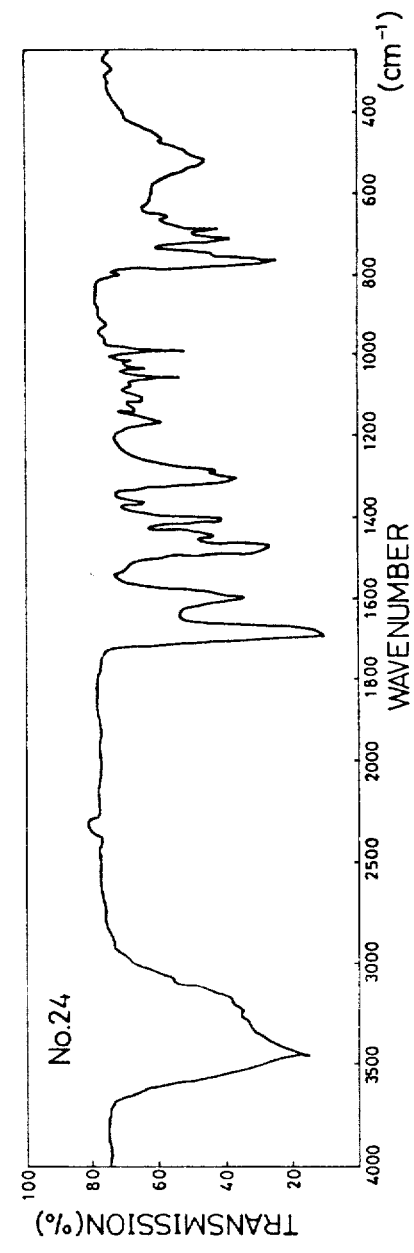
Figure 25:
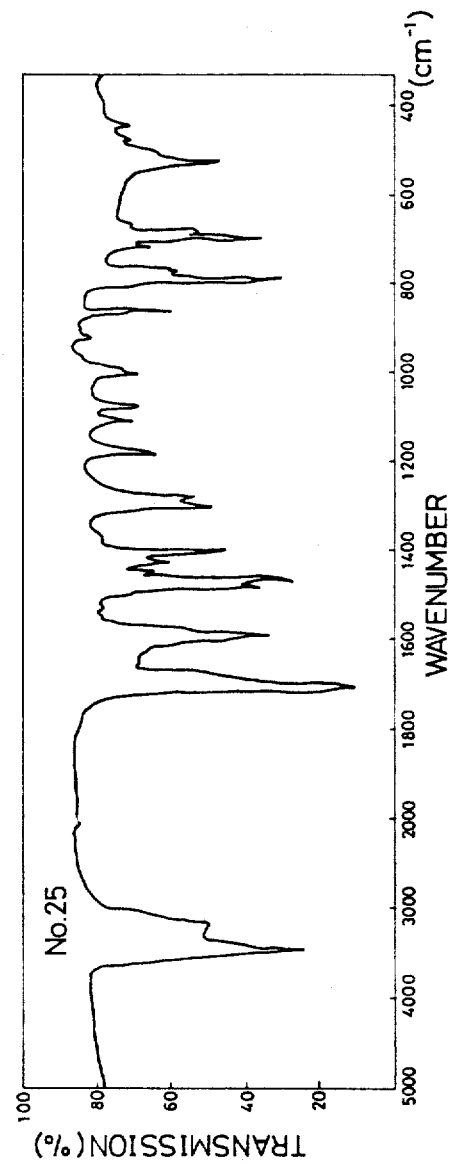
Figure 26:
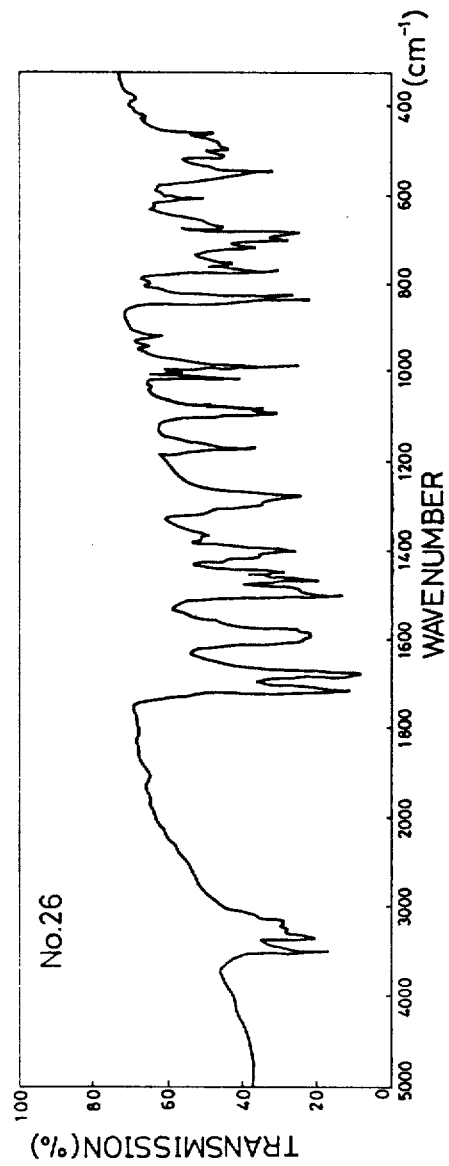
Figure 27:
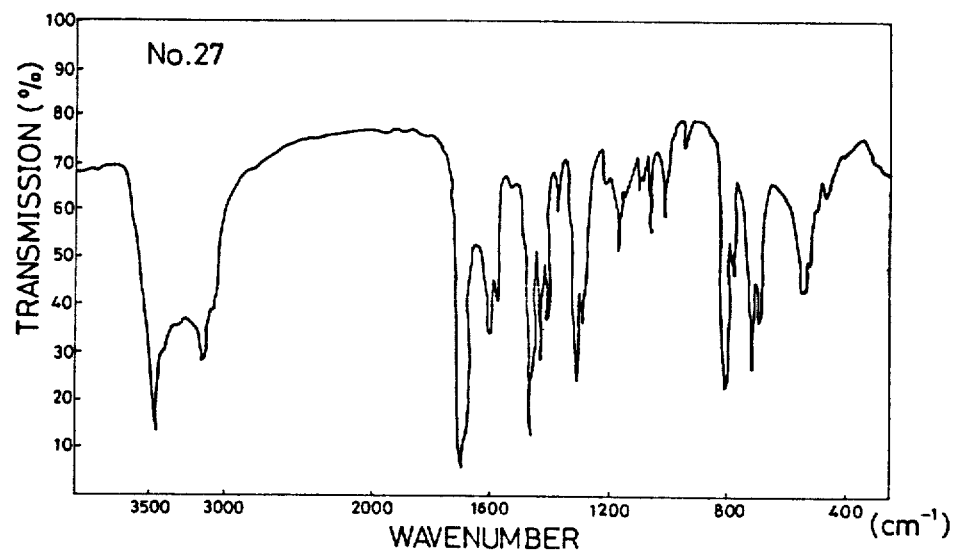
Figure 28:
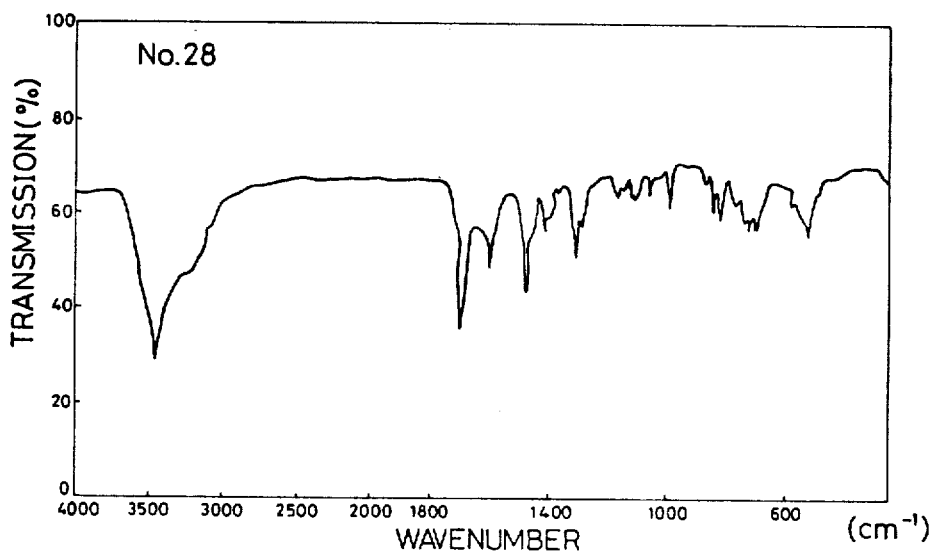
Figure 29:
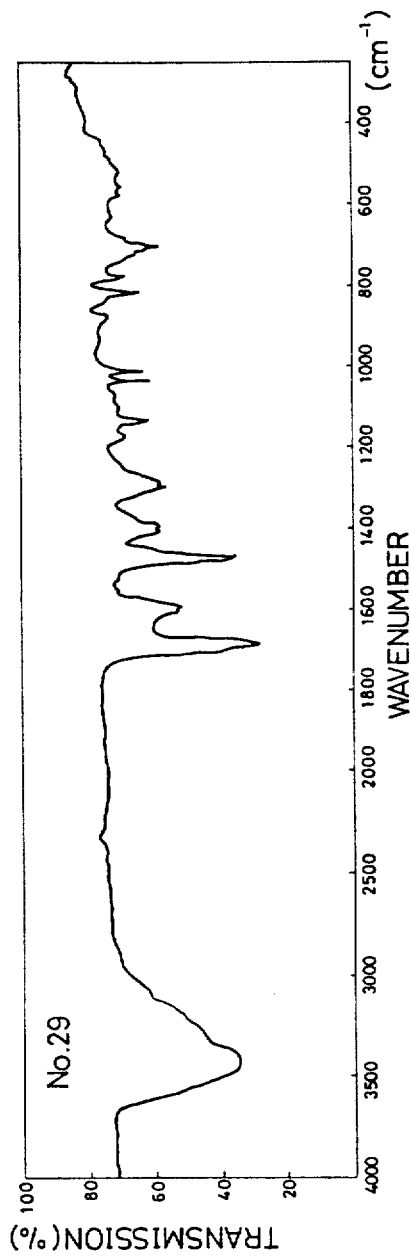
Figure 30:
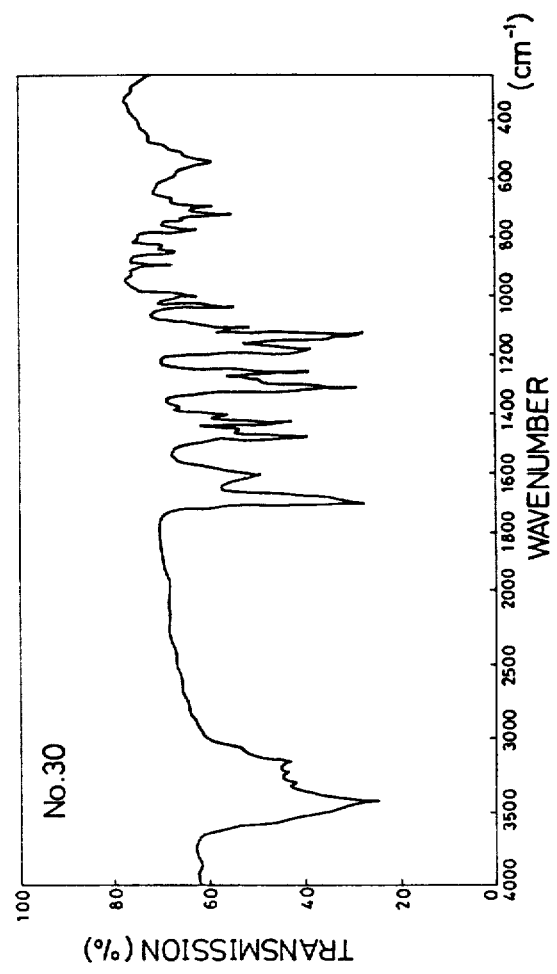
Figure 31:
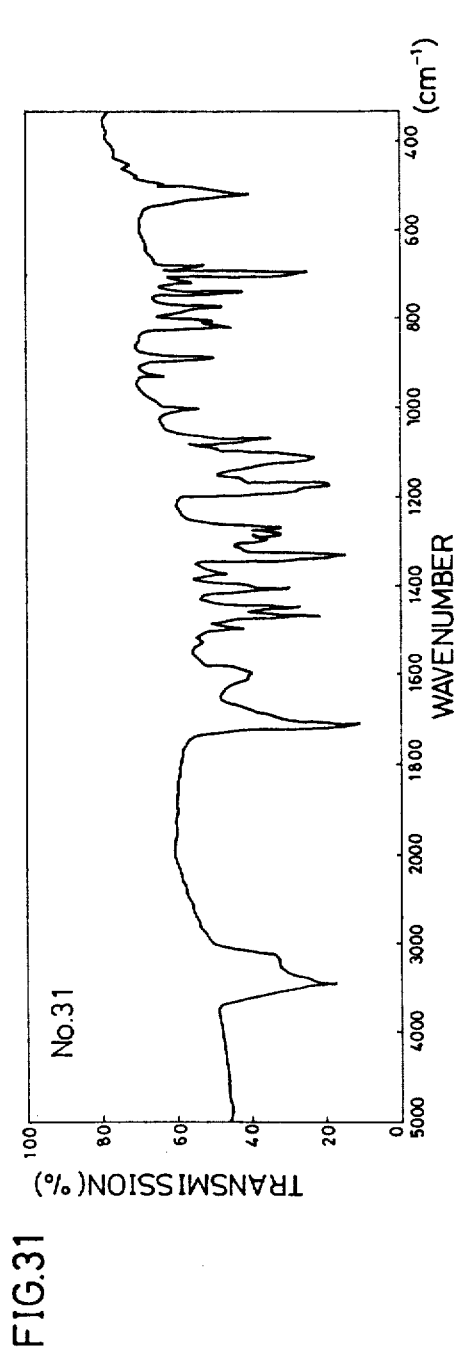
Figure 32:
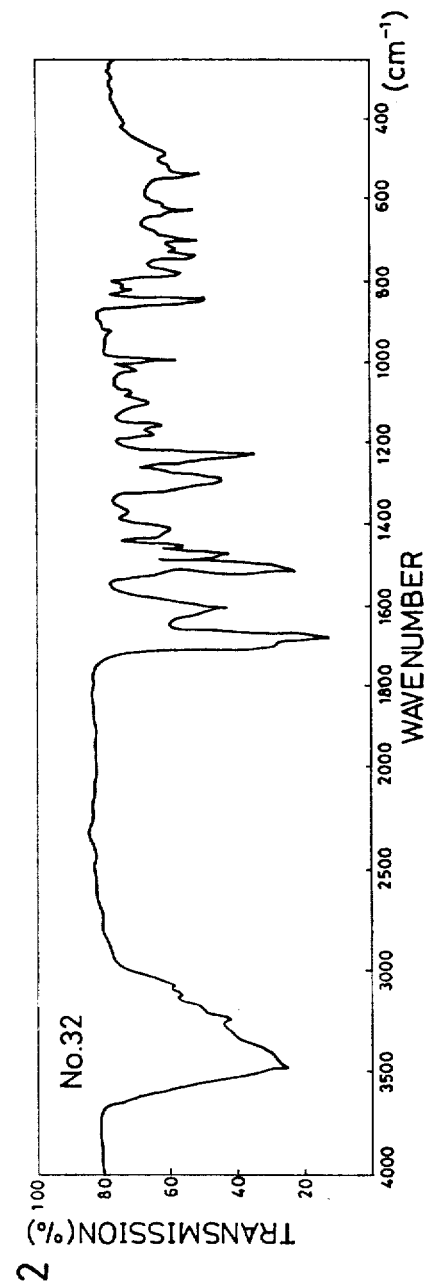
Figure 33:
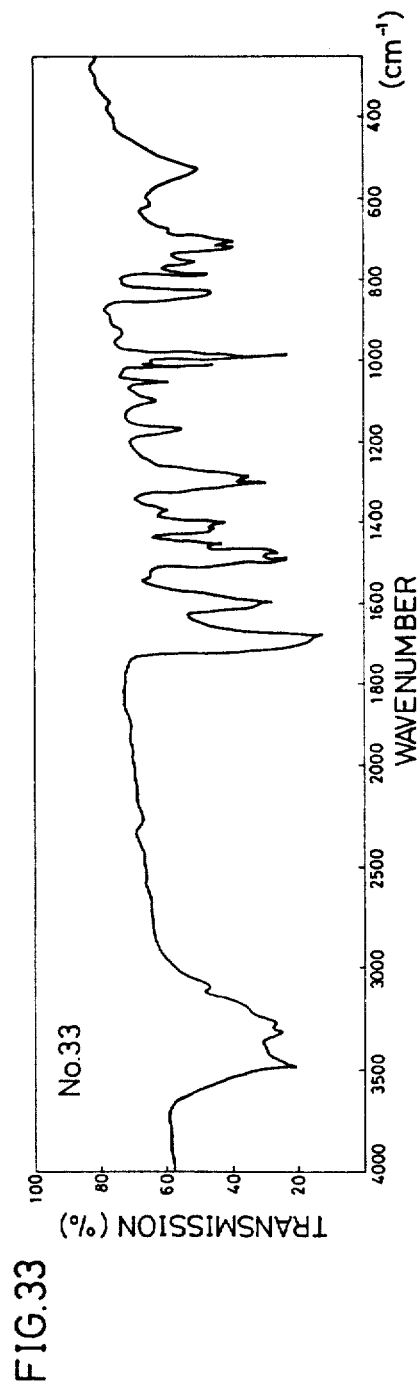
Figure 34:
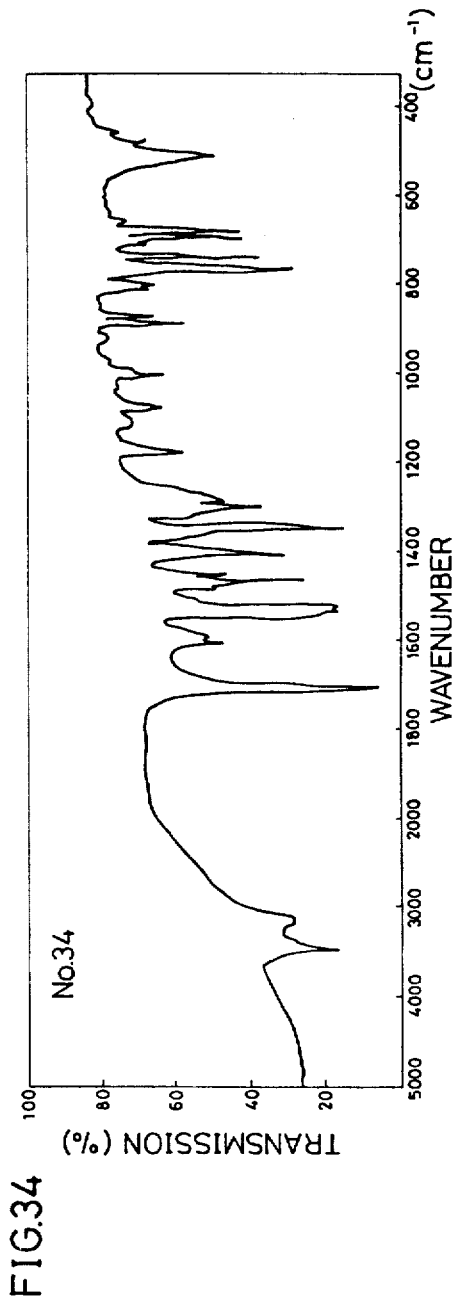

Examples of the compound of the invention are as follows (Table 1), in the Table melting point and the solvent used for recrystallization are also shown, the infrared absorption spectra of each compound are shown in FIGS. 1 to 34 corresponding to the No. of Table 1.

TABLE 1

| No. | | m.p. (°C.) | solvent |
|---|---|---|---|
| 1 | 1-(2-methylphenyl)-5-phenyl-1,2,4-triazole-3-carboxamide | 183–184 | $C_6H_6$ |
| 2 | 1-(3-methylphenyl)-5-phenyl-1,2,4-triazole-3-carboxamide | 142–143 | $CH_3OH-H_2O$ |
| 3 | 1-(2,3-dimethylphenyl)-5-phenyl-1,2,4-triazole-3-carboxamide | 186–188 | $CHCl_3$—$n$-$C_6H_{14}$ |
| 4 | 1-(2,4-dimethylphenyl)-5-phenyl-1,2,4-triazole-3-carboxamide | 197–199 | $CH_3OH$ |
| 5 | 1-(2,5-dimethylphenyl)-5-phenyl-1,2,4-triazole-3-carboxamide | 171–173 | $CH_3OH-H_2O$ |
| 6 | 1-(2,6-dimethylphenyl)-5-phenyl-1,2,4-triazole-3-carboxamide | 185.5–187 | $CH_3OH-H_2O$ |
| 7 | 1-(3,4-dimethylphenyl)-5-phenyl-1,2,4-triazole-3-carboxamide | 169–170 | $CH_3CH_2OH-H_2O$ |
| 8 | 1-(3,5-dimethylphenyl)-5-phenyl-1,2,4-triazole-3-carboxamide | 166–167.5 | $CHCl_3$—$n$-$C_6H_{14}$ |
| 9 | 1-(2,3,4-trimethylphenyl)-5-phenyl-1,2,4-triazole-3-carboxamide | 219–221 | $CH_3OH-H_2O$ |
| 10 | 1-(2,4,5-trimethylphenyl)-5-phenyl-1,2,4-triazole-3-carboxamide | 202–203.5 | $CH_3OH$ |
| 11 | 1-(3-ethylphenyl)-5-phenyl-1,2,4-triazole-3-carboxamide | 176.5–177 | $CH_3CH_2OH-H_2O$ |
| 12 | 1-(4-ethylphenyl)-5-phenyl-1,2,4-triazole-3-carboxamide | 199–201 | $CHCl_3$—$n$-$C_6H_{14}$ |
| 13 | 1-(3-n-propylphenyl)-5-phenyl-1,2,4-triazole-3-carboxamide | 120–121 | $CH_3OH-H_2O$ |
| 14 | 1-(4-n-propylphenyl)-5-phenyl-1,2,4-triazole-3-carboxamide | 185–186.5 | $(CH_3)_2CO$—$n$-$C_6H_{14}$ |
| 15 | 1-(4-i-propylphenyl)-5-phenyl-1,2,4-triazole-3-carbox- | 206–208 | $CHCl_3$—$n$-$C_6H_{14}$ |

TABLE 1-continued

| No. | | m.p. (°C) | solvent |
|---|---|---|---|
| | amide | | |
| 16 | 1-(2-methyl-3-chlorophenyl-5-phenyl-1,2,4-triazole-3-carboxamide | 198–200 | CH₃CH₂OH |
| 17 | 1-(2-chloro-3-methylphenyl)-5-phenyl-1,2,4-triazole-3-carboxamide | 170–171 | CH₃CH₂OH—H₂O |
| 18 | 1-(2-methyl-4-chlorophenyl-5-phenyl-1,2,4-triazole-3-carboxamide | 197–199 | CH₃OH—H₂O |
| 19 | 1-(2-chloro-4-methylphenyl-5-phenyl-1,2,4-triazole-3-carboxamide | 194–195.5 | CHCl₃—n-C₆H₁₄ |
| 20 | 1-(3-methyl-4-chlorylphenyl)-5-phenyl-1,2,4-triazole-3-carboxamide | 169–171 | CHCl₃—n-C₆H₁₄ |
| 21 | 1-(3-chloro-4-methylphenyl)-5-phenyl-1,2,4-triazole-3-carboxamide | 151–153 | CHCl₃—n-C₆H₁₄ |
| 22 | 1-(3-methyl-4-fluorophenyl)-5-phenyl-1,2,4-triazole-3-carboxamide | 123–126 | CH₃CH₂OH—H₂O |
| 23 | 1-(3-methyl-5-chlorophenyl)-5-phenyl-1,2,4-triazole-3-carboxamide | 163.5–165.5 | CHCl₃—n-C₆H₁₄ |
| 24 | 1-(2-chlorophenyl)-5-phenyl-1,2,4-triazole-3-carboxamide | 171–171.5 | CHCl₃—n-C₆H₁₄ |
| 25 | 1-(3-chlorophenyl)-5-phenyl-1,2,4-triazole-3-carboxamide | 179–180 (decompose) | C₆H₆ |
| 26 | 1-(4-chlorophenyl)-5-phenyl-1,2,4-triazole-3-carboxamide | 186–188 | CH₃OH |
| 27 | 1-(2,3-dichlorophenyl)-5-phenyl-1,2,4-triazole-3-carboxamide | 202–204 | CH₃OH—H₂O |
| 28 | 1-(2,4-dichlorophenyl)-5-phenyl-1,2,4-triazole-3-carboxamide | 211–212 | CH₃OH—H₂O |
| 29 | 1-(3,4-dichlorophenyl)-5-phenyl-1,2,4-triazole-3-carboxamide | 180–181 | CHCl₃—n-C₆H₁₄ |
| 30 | 1-(3-trifluoromethyl-4-chlorophenyl)-5-phenyl-1,2,4-triazole-3-carboxamide | 147–149 | CHCl₃—n-C₆H₁₄ |
| 31 | 1-(3-trifluoromethylphenyl)-5-phenyl-1,2,4-triazole-3-carboxamide | 195–197 | CHCl₃—n-C₆H₁₄ |
| 32 | 1-(4-fluorophenyl)-5-phenyl-1,2,4-triazole-3-carboxamide | 185–187 | CHCl₃—n-C₆H₁₄ |
| 33 | 1-(4-iodophenyl)-5-phenyl-1,2,4-triazole-3-carboxamide | 192–193 | CHCl₃—n-C₆H₁₄ |
| 34 | 1-(3-nitrophenyl)-5-phenyl-1,2,4-triazole-3-carboxamide | 217–219 | CH₃OH |

It is observed that the compound of the invention shows excellent herbicidal activities to broad-leaved plants and grasses, especially to common purslane (Portulaca oleracea), lambs quarters (Chenopodium album), common chickweed (Stellaria media), Wavy bittercress (Cardamine flexuosa) and smart weed (Polygonum longisetum), in herbicidal tests such as germination, soil treatment, foliage treatment, and the like without phytotoxicity to rice, wheat, corn, cotton, and the like as shown in Examples hereinafter.

Therefore, the compound of the invention may be employed for an active ingredient of a herbicide and may be applied to a farm such as a paddy and upland field and a fruit field or a flouriculture.

The compound of the invention may be singly applied or may be applied in the form of a composition diluted to a suitable concentration, for example 30 to 80 p.p.m. by weight, with a diluent used for the conventional herbicides by any appropriate procedure such as spraying onto an object. If necessary, a herbicidal composition of the invention may contain an adjuvant such as a spreader, a wettable agent and a fixing agent. Furthermore, the herbicidal composition may be combined or may be admixed with other physiologically active agent such as a fungicide, an insecticide, a herbicide and a plant growth regulator or a fertilizer, since the compound of the invention is not decomposed or denatured per se and does not decompose or denature other active agents.

An amount of the composition or compound of the invention applied may be varied in the wide range as the conventional herbicide, for example 100 to 300 g of the active ingredient (the compound of the invention) may be applied per 10 are of the field to be treated.

The invention will be further illustrated while referring to the non-limiting examples hereinafter described. From the foregoing description, one skilled in the art can easily ascertain the essential characteristics of this invention, and without departing from the spirit and scope thereof, can make various changes and modifications of the invention to adapt it to various usages and conditions.

PREPARATION 1

1-(3-methylphenyl)-5-phenyl-1H-1,2,4-triazole-3-carboxamide (Compound No. 2 of Table 1)

Three grams (0.01 mole) of 4-(3-methylphenylhydrazono)-2-phenyl-oxazoline-5-one ($R^1=3-CH_3$, $R^2=R^3=H$ in the formula II) was suspended in 93 ml of methanol. To the resulting suspension, 66.2 ml of 29% solution of ammonium hydroxide (0.549 mole) was added and refluxed for 5 minutes. Methanol and ammonia were then distilled off under a reduced pressure, and the resulting crystals were filtered out and washed with water. The crystals were recrystallized from a mixed solvent of 5.8 ml of methanol and 4.5 ml of water to obtain 1.8 g of almost colorless crystal, m.p. 142°–143° C., with a yield of 63%. I.R. (KBr, cm⁻¹, refer to FIG. 2); 3500–3240 (broad and strong), 1700, 1670, 1610, 1458, 1400, 1302, 789 and 700.

I.R. (liquid membrane, CHCl₃ solution); 3500 ($v_{NH_2}$) and 3400.

NMR (solvent; d₆-DMSO, δ, p.p.m.); 2.32 (3H, s,

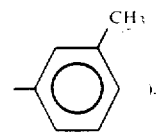

7.03–7.65 (9H, m, aromatic proton), 7.73, 7.96 (2H, s, —CONH₂), wherein s and m denote singlet and multiplet, respectively.

PREPARATION 2

1-(3,4-dimethylphenyl)-5-phenyl-1H-1,2,4-triazole-3-carboxamide (Compound No. 7 of Table 1)

Three grams (0.01 mole) of 4-(3,4-dimethylphenylhydrazono)-2-phenyl-oxazoline-5-one ($R^1$=3—$CH_3$, $R^2$=4—$CH_3$ and $R^3$=H in the formula II) was suspended in 16 ml of acetone. To the resulting suspension, 1.57 ml of 29% solution of $NH_4OH$ (0.013 mole) was added dropwise at room temperature. After refluxing for 25 minutes, heating was stopped and 1.57 ml of concentrated hydrochloric acid was added dropwise. The resulting mixture was again refluxed for 5 minutes. 42 ml of water was then added to the reaction mixture, and obtained crystal was filtered out, washed with acetone containing water and dried. The thus treated crystal was recrystallized from a mixture of 8.8 ml of ethanol and 3 ml of water to obtain 2.25 g of almost colorless crystal, m.p. 169°-170° C., with a yield of 76.9%.

I.R. (KBr, $cm^{-1}$, refer to FIG. 7); 3500, 3360, 3240, 1699 and 1670.

NMR (solvent; $d_6$-DMSO, δ, p.p.m.); 2.22 (3H, s,

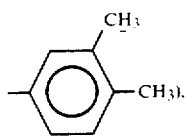

2.7 (3H, s,

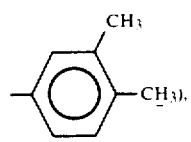

7.02–7.74 (8H, m, aromatic proton), 7.85, 8.05 (2H, s, —$CONH_2$).

PREPARATION 3

1-(2-methyl-3-chlorophenyl)-5-phenyl-1H-1,2,4-triazole-3-carboxamide (Compound No. 16 of Table 1)

6.2 g (0.019 mole) of 4-(2-methyl-3-chlorophenylhydrazono)-2-phenyl-oxazoline-5-one ($R^1$=2—$CH_3$, $R^2$=3—Cl and $R^3$=H in the formula II) was added to 60 ml of acetone with stirring. To the resulting mixture, 3 ml of 29% solution of $NH_4OH$ (0.024 mole) was added dropwise at room temperature. Then the mixture was refluxed for 25 minutes and heating was stopped. After 3 ml of concentrated hydrochloric acid was added dropwise, and then the mixture was refluxed again for 5 minutes. The obtained reaction mixture was filtered while hot, and 80 ml of water was added to the filtrate. The obtained mixture was allowed to stand for cooling to obtain a product. The product was filtered out, washed with acetone containing water and dried. The crystal was recrystallized from 60 ml of ethanol to obtain 4.8 g of almost colorless crystal, m.p. 198°-200° C., with a yield of 78.2%.

I.R. (KBr, $cm^{-1}$, refer to FIG. 16); 1680, 1470, 1300 and 780.

NMR (solvent; $d_6$-DMSO, δ, p.p.m.); 1.98 (3H, s,

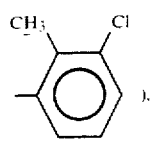

7.35–7.8 (8H, m, aromatic proton), 7.85, 8.1 (2H, s, —$CONH_2$).

PREPARATION 4

1-(3-methyl-4-fluorophenyl)-5-phenyl-1H-1,2,4-triazole-3-carboxamide (Compound No. 22 of Table 1)

3.0 g (0.01 mole) of 4-(3-methyl-4-fluorophenylhydrazono)-2-phenyl-oxazoline-5-one ($R^1$=3—$CH_3$, $R^2$=4—F and $R^3$=H in the formula II) was suspended in 16 ml of acetone. To the suspension, 1.57 ml of 29% solution of $NH_4OH$ (0.013 mole) was added dropwise at room temperature. After refluxing the reaction mixture for 25 minutes, heating was stopped and 1.57 ml of concentrated hydrochloric acid was added dropwise. After the addition was over, the reaction mixture was refluxed again for 5 minutes. Then 40 ml of water was added to the reaction mixture, and the resulting crystal was filtered out, washed with acetone containing water and dried. The obtained crystal was recrystallized from a mixture of 20 ml of ethanol and 5 ml of water to obtain 1.7 g of almost colorless crystal, m.p. 123°-126° C., with a yield of 55.2%.

I.R. (KBr, $cm^{-1}$, refer to FIG. 22); 1690, 1660, 1490, 1400, 1300, 1290, 1230, 1190, 1000, 740 and 690.

NMR (solvent; $d_6$-DMSO, δ, p.p.m.); 2.37 (3H, d, J=2Hz,

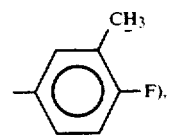

7.35–7.8 (8H, m, aromatic proton), 7.85 and 8.10 (2H, s, —$CONH_2$), wherein d and J denotes doublet and coupling constant, respectively, and s and m are defined above.

FORMULATION 1

Wettable powder

| Component | Parts by weight |
|---|---|
| Compound No. 2 | 50 |
| ligninsulfonate | 5 |
| alkylsulfonate | 3 |
| diatomaceous earth | 42 |

These components were mixed and pulverized to obtain a wettable powder which may be applied after diluting with water.

FORMULATION 2

Emulsion

| Component | Parts by weight |
|---|---|
| Compound No. 7 | 25 |
| xylene | 65 |

-continued

| Component | Parts by weight |
|---|---|
| polyoxyethylene alkyl aryl ether | 10 |

These components were uniformly mixed to obtain an emulsifiable formulation which may be applied after diluting with water.

FORMULATION 3

Granulation

| Component | Parts by weight |
|---|---|
| Compound No. 16 | 8 |
| bentonite | 40 |
| clay | 45 |
| ligninsulfonate | 7 |

These components were uniformly mixed, kneaded with water, granulated from an extrusion granulator and dried to obtain a granule.

The effectiveness of the compound of the invention as a herbicide is illustrated while referring to the examples as follows.

EXAMPLE 1

Germination

In each glass dish of 9 cm in diameter, 2 sheets of filter paper were placed in layers. After pouring 5 ml of an aqueous suspension of each compound of the invention (concentration of the active ingredient being 25 or 50 ppm) on the filter paper, 15 seeds of each test plant shown in Table 2 were placed on the filter paper. The thus prepared dishes were placed in a room at a controlled temperature of 25° C. under light condition. After 4 days of placing, the state of germination of the seeds was investigated, and after leaving the dishes for further six days as they were, the state of growth-inhibition of the germinated weeds and the crop plants was observed by naked eyes and judged according to the standard scale from 0 (corresponding to no inhibition) to 5 (no germination or withered after germination). The results of observation were shown in Table 2.

TABLE 2

| Concentration (ppm) | Compound No. | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | 1 | | 2 | | 3 | | 4 | | 5 | | 6 | | 7 | | 8 | | 9 | | 10 | | 11 | | 12 | | 13 | | 14 | |
| | 25 | 50 | 25 | 50 | 25 | 50 | 25 | 50 | 25 | 50 | 25 | 50 | 25 | 50 | 25 | 50 | 25 | 50 | 25 | 50 | 25 | 50 | 25 | 50 | 25 | 50 | 25 | 50 |
| Oryza sativa | 1 | 3 | 4 | 5 | 1 | 4 | 2 | 2 | 0 | 1 | 0 | 0 | 3 | 5 | 0 | 0 | 1 | 1 | 1 | 1 | 2 | 4 | 0 | 1 | 2 | 2 | 0 | 1 |
| Echinochloa crus-galli var. frumentacea | 2 | 3 | 5 | 5 | 3 | 5 | 5 | 5 | 1 | 2 | 0 | 0 | 4 | 5 | 0 | 0 | 2 | 3 | 2 | 2 | 3 | 4 | 0 | 1 | 2 | 2 | 0 | 0 |
| Cyperus iria | 0 | 1 | 4 | 5 | 3 | 5 | 3 | 5 | 1 | 2 | 2 | 4 | 5 | 5 | 1 | 3 | 2 | 2 | 1 | 1 | 5 | 5 | 0 | 1 | 1 | 1 | 0 | 0 |
| Portulaca oleracea | 5 | 5 | 5 | 5 | 5 | 5 | 5 | 5 | 5 | 5 | 2 | 3 | 5 | 5 | 5 | 5 | 2 | 5 | 5 | 5 | 5 | 5 | 2 | 5 | 5 | 5 | 5 | 5 |
| Chenopodium album | 5 | 5 | 5 | 5 | 5 | 5 | 5 | 5 | 5 | 5 | 2 | 2 | 5 | 5 | 5 | 5 | 5 | 5 | 5 | 5 | 5 | 5 | 3 | 5 | 5 | 5 | 5 | 5 |

| Concentration (ppm) | Compound No. | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | 15 | | 16 | | 17 | | 18 | | 19 | | 20 | | 21 | | 22 | | 23 | | 24 | | 25 | | 26 | | 27 | | 28 | |
| | 25 | 50 | 25 | 50 | 25 | 50 | 25 | 50 | 25 | 50 | 25 | 50 | 25 | 50 | 25 | 50 | 25 | 50 | 25 | 50 | 25 | 50 | 25 | 50 | 25 | 50 | 25 | 50 |
| Oryza sativa | 1 | 1 | 5 | 5 | 4 | 5 | 0 | 0 | 0 | 0 | 4 | 4 | 4 | 4 | 4 | 1 | 3 | 3 | 3 | 3 | 4 | 0 | 4 | 0 | 3 | 1 | 0 |
| Echinochloa crus-galli var. frumentacea | 1 | 1 | 5 | 5 | 5 | 5 | 1 | 4 | 0 | 2 | 4 | 4 | 3 | 4 | 4 | 5 | 0 | 1 | 0 | 2 | 2 | 2 | 1 | 4 | 1 | 4 | 1 | 1 |
| Cyperus iria | 0 | 0 | 4 | 5 | 4 | 5 | 0 | 2 | 1 | 3 | 5 | 5 | 3 | 4 | 5 | 5 | 0 | 2 | 1 | 1 | 1 | 3 | 0 | 2 | 1 | 2 | 0 | 1 |
| Portulaca oleracea | 0 | 1 | 5 | 5 | 5 | 5 | 5 | 5 | 5 | 5 | 5 | 5 | 5 | 5 | 5 | 5 | 3 | 5 | 5 | 5 | 5 | 5 | 5 | 5 | 5 | 5 | 5 | 5 |
| Chenopodium album | 1 | 3 | 5 | 5 | 5 | 5 | 5 | 5 | 3 | 5 | 5 | 5 | 5 | 5 | 5 | 5 | 5 | 5 | 3 | 5 | 5 | 5 | 5 | 5 | 5 | 5 | 2 | 2 |

| Concentration (ppm) | Compound No. | | | | | | | | | | | Control |
|---|---|---|---|---|---|---|---|---|---|---|---|---|
| | 29 | | 30 | | 31 | | 32 | | 33 | | 34 | | |
| | 25 | 50 | 25 | 50 | 25 | 50 | 25 | 50 | 25 | 50 | 25 | 50 | — |
| Oryza sativa | 0 | 2 | 1 | 1 | 0 | 2 | 0 | 0 | 0 | 1 | 0 | 1 | 0 |
| Echinochloa crus-galli var. frumentacea | 0 | 1 | 0 | 0 | 1 | 2 | 2 | 2 | 0 | 0 | 0 | 0 | 0 |
| Cyperus iria | 1 | 2 | 0 | 0 | 0 | 1 | 0 | 1 | 0 | 1 | 0 | 0 | 0 |
| Portulaca oleracea | 5 | 5 | 2 | 2 | 5 | 5 | 3 | 5 | 1 | 2 | 3 | 5 | 0 |
| Chenopodium album | 5 | 5 | 2 | 3 | 5 | 5 | 5 | 5 | 3 | 5 | 2 | 5 | 0 |

EXAMPLE 2

Soil treatment before germination

Into a planter of 650 mm in length, 210 mm in width and 200 mm in height, soil taken from a farm land was placed, and a predetermined amount of seeds of each one of weeds and crop plants shown in Table 3 was sown. After one day of covering the sown seeds thinly with light soil, 30 ml of an aqueous suspension of each compound of the invention was sprayed on the whole surface of the soil in the planter (corresponding to 300 g of the compound to be sprayed on 10 are of the soil surface). After 35 days of the spraying, the inhibiting effect of each compound on the growth of the weed and the phytotoxicity of each compound on the crop plant were observed by naked eyes, and the result of observation was converted into one of the indices shown below by the following standards, and is shown in Table 3.

| Standards |  |
|---|---|
| (1) Effect of inhibiting the growth of weeds: | |
| Index | Result of observation |
| 0 | no inhibition |
| 1 | extent of inhibition of 20% |
| 2 | extent of inhibition of 40% |
| 3 | extent of inhibition of 60% |
| 4 | extent of inhibition of 80% |
| 5 | complete inhibition |
| (2) Phytotoxicity to crop plants: | |
| Index | Result of observation |
| 0 | no harm |
| 1 | very slight harm |
| 2 | slight harm |
| 3 | moderate harm |
| 4 | severe harm |
| 5 | whitered or not germinated |

EXAMPLE 3

Soil treatment after germination

Into a planter of the same size as that used in Example 2, soil taken from a farm land was placed, and a predetermined amount of seeds of each one of weeds and crop plants shown in Table 3 was sown and the planter was left to stand for a period after which the germinated plants reached to their 2 to 3-true leaf stage. Then, aqueous suspension of each compound of the invention (corresponding to 300 g/10 are of the surface area of the soil in the planter) was sprayed uniformly onto the surface of the soil in the planter including the young plants therein. After 35 days of the spraying, the state of growth-inhibition of the weeds and the extent of phytotoxicity to the crop plants were observed by naked eyes. The result of observation was expressed by the following indices according to the standards shown in Example 2, and shown in Table 4.

TABLE 3

| Compound No. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| Oryza sativa | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Triticum sativum | 0 | 1 | 0 | 0 | 0 | 0 | 0 | 0 | 0 | 0 | 0 | 0 | 0 | 0 | 0 | 1 | 1 | 0 | 0 | 2 | 2 | 1 | 0 | 0 | 0 | 0 |
| Zea mays | 0 | 0 | 0 | 0 | 0 | 0 | 2 | 0 | 0 | 0 | 1 | 0 | 0 | 0 | 0 | 1 | 0 | 0 | 0 | 1 | 0 | 0 | 0 | 0 | 0 | 0 |
| Glycine soja | 3 | 5 | 3 | 2 | 2 | 1 | 5 | 2 | 0 | 1 | 3 | 1 | 3 | 2 | 0 | 4 | 4 | 3 | 3 | 4 | 5 | 3 | 1 | 3 | 3 | 3 |
| Gossypium arboreum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Digitaria sanguinalis | 1 | 4 | 3 | 3 | 2 | 0 | 4 | 0 | 0 | 0 | 3 | 2 | 1 | 1 | 0 | 4 | 3 | 3 | 3 | 4 | 4 | 4 | 0 | 3 | 2 | 2 |
| Poa annua | 1 | 5 | 5 | 4 | 5 | 0 | 5 | 0 | 0 | 0 | 5 | 3 | 1 | 0 | 0 | 5 | 5 | 4 | 3 | 5 | 5 | 4 | 2 | 0 | 3 | 3 |
| Stellaria media | 4 | 5 | 5 | 5 | 5 | 1 | 5 | 5 | 1 | 1 | 5 | 5 | 2 | 1 | 1 | 5 | 5 | 5 | 5 | 5 | 5 | 5 | 2 | 4 | 5 | 4 |
| Cardamine flexuosa | 4 | 5 | 5 | 5 | 5 | 2 | 5 | 5 | 1 | 1 | 5 | 5 | 3 | 2 | 1 | 5 | 5 | 5 | 5 | 5 | 5 | 5 | 1 | 0 | 5 | 5 |
| Portulaca oleracea | 4 | 5 | 5 | 5 | 5 | 1 | 5 | 4 | 1 | 1 | 5 | 5 | 2 | 1 | 1 | 5 | 5 | 5 | 5 | 5 | 5 | 5 | 2 | 3 | 4 | 4 |
| Chenopodium album | 3 | 5 | 5 | 5 | 5 | 1 | 5 | 5 | 0 | 0 | 4 | 4 | 2 | 0 | 0 | 5 | 5 | 4 | 4 | 5 | 5 | 5 | 1 | 5 | 4 | 4 |
| Polygonum longisetum | 4 | 5 | 4 | 4 | 4 | 0 | 5 | 5 | 0 | 0 | 4 | 3 | 1 | 0 | 0 | 5 | 5 | 4 | 3 | 5 | 5 | 4 | 1 | 5 | 4 | 4 |

| Compound No. | 27 | 28 | 29 | 30 | 31 | 32 | 33 | 34 | Control |
|---|---|---|---|---|---|---|---|---|---|
| Oryza sativa | 0 | 0 | 0 | 0 | 0 | 0 | 0 | 0 | 0 |
| Triticum sativum | 0 | 0 | 0 | 0 | 1 | 2 | 0 | 0 | 0 |
| Zea mays | 0 | 0 | 0 | 1 | 0 | 1 | 0 | 0 | 0 |
| Glycine soja | 3 | 2 | 4 | 3 | 2 | 3 | 0 | 1 | 0 |
| Gossypium arboreum | 0 | 0 | 0 | 0 | 0 | 0 | 0 | 0 | 0 |
| Digitaria sanguinalis | 2 | 3 | 3 | 4 | 3 | 3 | 2 | 0 | 0 |
| Poa annua | 2 | 4 | 5 | 4 | 4 | 1 | 0 | 0 | 0 |
| Stellaria media | 4 | 5 | 5 | 5 | 5 | 5 | 0 | 1 | 0 |
| Cardamine flexuosa | 4 | 5 | 5 | 5 | 5 | 5 | 0 | 0 | 0 |
| Portulaca oleracea | 4 | 5 | 5 | 5 | 5 | 5 | 1 | 1 | 0 |
| Chenopodium album | 3 | 4 | 5 | 5 | 5 | 5 | 0 | 0 | 0 |
| Polygonum longisetum | 3 | 4 | 5 | 5 | 4 | 5 | 1 | 0 | 0 |

TABLE 4

| Compound No. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| Oryza sativa | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Triticum sativum | 0 | 0 | 0 | 0 | 1 | 0 | 2 | 0 | 0 | 0 | 1 | 0 | 0 | 0 | 0 | 1 | 0 | 0 | 0 | 2 | 0 | 0 | 0 | 0 | 2 | 0 |
| Zea mays | 0 | 1 | 1 | 0 | 1 | 0 | 0 | 1 | 0 | 0 | 1 | 0 | 0 | 0 | 0 | 1 | 1 | 1 | 0 | 1 | 1 | 1 | 0 | 0 | 1 | 0 |
| Glycine soja | 4 | 5 | 4 | 3 | 3 | 2 | 5 | 3 | 1 | 2 | 4 | 4 | 1 | 1 | 1 | 5 | 4 | 3 | 4 | 3 | 5 | 5 | 2 | 2 | 4 | 2 |
| Gossypium arboreum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Digitaria sanguinalis | 0 | 2 | 3 | 2 | 1 | 0 | 5 | 4 | 0 | 0 | 2 | 1 | 0 | 0 | 1 | 3 | 3 | 2 | 2 | 3 | 2 | 3 | 0 | 4 | 0 | 1 |
| Poa annua | 0 | 4 | 3 | 3 | 4 | 1 | 5 | 0 | 0 | 1 | 3 | 1 | 0 | 2 | 1 | 5 | 3 | 2 | 3 | 4 | 2 | 2 | 1 | 0 | 1 | 3 |
| Stellaria media | 3 | 5 | 4 | 4 | 5 | 2 | 5 | 3 | 2 | 2 | 4 | 2 | 2 | 2 | 2 | 5 | 5 | 5 | 5 | 5 | 5 | 5 | 3 | 3 | 4 | 3 |
| Cardamine flexuosa | 3 | 5 | 5 | 4 | 5 | 2 | 5 | 3 | 2 | 2 | 4 | 2 | 2 | 2 | 2 | 5 | 5 | 5 | 5 | 5 | 5 | 5 | 3 | 3 | 4 | 3 |
| Portulaca oleracea | 4 | 5 | 5 | 4 | 4 | 3 | 5 | 1 | 1 | 2 | 4 | 2 | 1 | 1 | 2 | 5 | 5 | 3 | 4 | 5 | 5 | 5 | 2 | 0 | 3 | 2 |
| Chenopodium album | 3 | 5 | 5 | 5 | 5 | 2 | 5 | 1 | 2 | 2 | 4 | 3 | 1 | 0 | 0 | 5 | 5 | 4 | 4 | 5 | 5 | 5 | 2 | 0 | 3 | 4 |
| Polygonum longisetum | 3 | 5 | 5 | 4 | 4 | 2 | 5 | 2 | 2 | 1 | 3 | 3 | 1 | 0 | 0 | 5 | 5 | 4 | 4 | 5 | 5 | 5 | 3 | 2 | 3 | 3 |

| Compound No. | 27 | 28 | 29 | 30 | 31 | 32 | 33 | 34 | Control |
|---|---|---|---|---|---|---|---|---|---|
| Oryza sativa | 0 | 0 | 0 | 0 | 0 | 0 | 0 | 0 | 0 |
| Triticum sativum | 0 | 0 | 0 | 2 | 1 | 0 | 0 | 0 | 0 |
| Zea mays | 1 | 0 | 0 | 1 | 1 | 0 | 1 | 0 | 0 |
| Glycine soja | 3 | 3 | 3 | 5 | 5 | 4 | 1 | 0 | 0 |
| Gossypium arboreum | 0 | 0 | 0 | 0 | 0 | 0 | 0 | 0 | 0 |
| Digitaria sanguinalis | 1 | 2 | 3 | 4 | 2 | 4 | 0 | 0 | 0 |
| Poa annua | 2 | 3 | 2 | 3 | 2 | 0 | 0 | 0 | 0 |
| Stellaria media | 5 | 5 | 5 | 5 | 5 | 5 | 1 | 2 | 0 |
| Cardamine flexuosa | 5 | 5 | 5 | 5 | 5 | 5 | 0 | 1 | 0 |
| Portulaca oleracea | 4 | 3 | 5 | 5 | 4 | 5 | 0 | 0 | 0 |

TABLE 4-continued

| | | | | | | | | | |
|---|---|---|---|---|---|---|---|---|---|
| Chenopodium album | 3 | 4 | 5 | 5 | 4 | 0 | 0 | 0 | 0 |
| Polygonum longisetum | 4 | 3 | 5 | 4 | 4 | 1 | 0 | 0 | 0 |

EXAMPLE 4

Foilage treatment

To the leaves and stems of 4 species of weeds grown in an unglazed porcelain pot containing soil from a farm land at their 2 to 3 leaf-stage, an aqueous suspension of each compound of the invention at a concentration of 1000 ppm was sprayed and the weeds were cultured, and after 14 days of the spraying, the herbicidal effect on the weeds was observed by naked eyes, and the results are expressed by one of the indices used in Example 2, and shown in Table 5

TABLE 5

| Compound No. | 1 | 2 | 3 | 4 | 5 | 6 | 7 | 8 | 9 | 10 |
|---|---|---|---|---|---|---|---|---|---|---|
| Poa annua | 0 | 3 | 0 | 0 | 0 | 0 | 0 | 0 | 0 | 0 |
| Stellaria media | 5 | 5 | 3 | 2 | 3 | 0 | 3 | 3 | 0 | 0 |
| Portulaca oleracea | 5 | 5 | 3 | 2 | 5 | 2 | 3 | 5 | 0 | 0 |
| Cardamine flexuosa | 5 | 5 | 5 | 4 | 4 | 0 | 4 | 3 | 0 | 0 |
| Compound No. | 11 | 12 | 13 | 14 | 15 | 16 | 17 | 18 | 19 | 20 |
| Poa annua | 0 | 0 | 0 | 0 | 0 | 2 | 3 | 0 | 0 | 0 |
| Stellaria media | 2 | 0 | 5 | 0 | 0 | 4 | 5 | 4 | 3 | 3 |
| Portulaca oleracea | 3 | 4 | 5 | 1 | 3 | 5 | 2 | 4 | 4 | 4 |
| Cardamine flexuosa | 4 | 1 | 5 | 0 | 0 | 5 | 5 | 5 | 4 | 4 |
| Compound No. | 21 | 22 | 23 | 24 | 25 | 26 | 27 | 28 | 29 | 30 |
| Poa annua | 0 | 0 | 0 | 0 | 0 | 0 | 0 | 0 | 0 | 1 |
| Stellaria media | 5 | 5 | 1 | 1 | 2 | 3 | 4 | 4 | 4 | 5 |
| Portulaca oleracea | 5 | 5 | 2 | 2 | 3 | 3 | 3 | 3 | 3 | 5 |
| Cardamine flexuosa | 5 | 5 | 1 | 3 | 5 | 4 | 3 | 4 | 4 | 4 |
| Compound No. | 31 | 32 | 33 | 34 | Control | | | | | |
| Poa annua | 0 | 0 | 0 | 0 | 0 | | | | | |
| Stellaria media | 3 | 3 | 0 | 3 | 0 | | | | | |
| Portulaca oleracea | 4 | 3 | 0 | 0 | 0 | | | | | |
| Cardamine flexuosa | 4 | 4 | 0 | 4 | 0 | | | | | |

What is claimed is:

1. A 1,5- disubstituted 1,2,4-triazole-3-carboxamide having the formula:

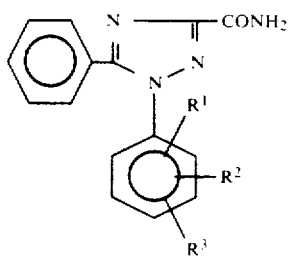

wherein $R^1$ is an atom of fluorine or chlorine, a methyl group or a trifluoromethyl group; $R^2$ is an atom of chlorine or a methyl group; and $R^3$ is an atom of hydrogen or a methyl group.

2. 1-(3,4-dimethylphenyl)-5-phenyl-1,2,4-triazole-3-carboxamide.

3. 1-(2-methyl-3-chlorophenyl)-5-phenyl-1,2,4-triazole-3-carboxamide.

4. 1-(2-chloro-3-methylphenyl)-5-phenyl-1,2,4-triazole-3-carboxamide.

5. 1-(3-methyl-4-chlorophenyl)-5-phenyl-1,2,4,-triazole-3-carboxamide.

6. 1-(3-chloro-4-methylphenyl)-5-phenyl-1,2,4-triazole-3-carboxamide.

7. 1-(3-methyl-4-fluorophenyl)-5-phenyl-1,2,4-triazole-3-carboxamide.

8. A herbicide composition comprising as an active ingredient a herbicidally effective amount of a 1,5-disubstituted 1,2,4-triazole-3-carboxamide represented by the formula:

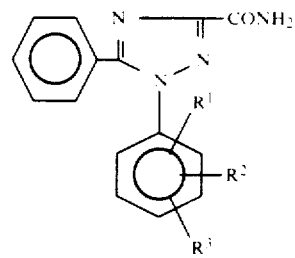

wherein $R^1$ is an alkyl group having 1 to 3 carbon atoms, a trifluoromethyl group, a chlorine atom, fluorine atom, an iodine atom or a nitro group, $R^2$ is a methyl group or a chlorine atom and $R^3$ is a methyl group or a hydrogen atom, provided that 1-(4-methylphenyl)-5-phenyl-1,2,4-triazole-3-carboxamide is excluded, together with a herbicidally acceptable carrier or a diluent.

9. The herbicide composition according to claim 8 in which the 1,5-disubstituted 1,2,4-triazole-3-carboxamide is 1-(3-methylphenyl)-5-phenyl-1,2,4-triazole-3-carboxamide.

10. A method for controlling noxious weeds, which comprises applying to said noxious weeds or to land a herbicide composition comprising as an active ingredient a herbicidally effective amount of a 1,5-disubstituted 1,2,4-triazole-3-carboxamide represented by the formula:

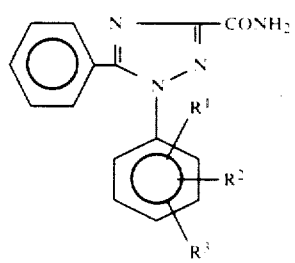

wherein $R^1$ is an alkyl group having 1 to 3 carbon atoms, a trifluoromethyl group, a chlorine atom, a fluorine atom, an iodine atom or a nitro group; $R^2$ is a methyl group or a chlorine atom and $R^3$ is a methyl group or a hydrogen atom, provided that 1-(4-methylphenyl)-5-phenyl-1,2,4-triazole-3-carboxamide is excluded, together with a herbicidally acceptable carrier or a diluent.

11. The method according to claim 10 in which said carboxamide is 1-(3-methyl-phenyl)-5-phenyl-1,2,4-triazole-3-carboxamide.

* * * * *